US009651525B2

(12) United States Patent
Grimard et al.

(10) Patent No.: US 9,651,525 B2
(45) Date of Patent: May 16, 2017

(54) METHOD AND APPARATUS FOR SCANNING AN OBJECT

(71) Applicant: TecScan Systems Inc., Boucherville (CA)

(72) Inventors: Nicolas Grimard, Montreal (CA); Rene Sicard, Brossard (CA); Sam H. Serhan, Brossard (CA)

(73) Assignee: TECSCAN SYSTEMS INC., Boucherville, Quebec (CA)

( * ) Notice: Subject to any disclaimer, the term of this patent is extended or adjusted under 35 U.S.C. 154(b) by 371 days.

(21) Appl. No.: 14/315,901

(22) Filed: Jun. 26, 2014

(65) Prior Publication Data

US 2015/0000410 A1    Jan. 1, 2015

Related U.S. Application Data

(60) Provisional application No. 61/840,047, filed on Jun. 27, 2013.

(51) Int. Cl.
*G06K 9/00* (2006.01)
*G01N 29/265* (2006.01)

(52) U.S. Cl.
CPC ... *G01N 29/265* (2013.01); *G01N 2291/2638* (2013.01); *G06K 9/00* (2013.01)

(58) Field of Classification Search
CPC ... A61F 11/08; H04R 1/1016; H04R 2225/77; H04R 25/652; H04R 25/658; H04R 2460/11; G01N 2291/2638; G01N 29/265; G01N 29/262; G01N 2291/051; G01N 2291/2634; G01N 29/0645; G01N 21/9515; G01N 21/952; G01N 21/954; G01N 2291/0423; G01N 29/041; G01N 29/07; G01N 29/2418; G01N 29/221;

(Continued)

(56) References Cited

U.S. PATENT DOCUMENTS 4,362,058 A * 12/1982 Abele ............. A61B 8/00
                                                    73/599
5,024,093 A *  6/1991 Sasaki .......... G01N 29/262
                                                    73/633

(Continued)

FOREIGN PATENT DOCUMENTS

CA    2790481 A1   3/2013
EP    1676128 B1   2/2008
(Continued)

*Primary Examiner* — Vu Le
*Assistant Examiner* — Aklilu Woldemariam
(74) *Attorney, Agent, or Firm* — BCF LLP

(57) ABSTRACT

The present disclosure relates to a method and an apparatus for scanning an object. Two virtual, orthogonal axes are positioned on a surface of the object. A scanning path of a moving probe is controlled as a function of the two virtual, orthogonal axes. The scanning path can include a plurality of probe positions determined according to a desired coverage of the object. A single probe can be used or, optionally, a pair of probes or an array of probes can be used, optionally mounting the probes on a multi-axis movable support. Optionally, a computer-aided design representing the object can be used to parameterize the object. The method and apparatus can be used to create an image of the object for non-destructive testing.

21 Claims, 11 Drawing Sheets

(58) Field of Classification Search
CPC ...... G01N 29/225; G01N 29/24; G01N 29/26;
G01N 29/4463; G06F 19/3437; G06F
19/3481; G06F 3/04815; A61B 8/4461;
A61B 2090/378; A61B 8/4254; A61B
8/4209; G01S 15/8925; G01S 15/8934;
G01S 15/8918; G01S 7/5205; G10K
11/355; G10K 11/352; B25J 13/088;
G01B 11/03; G01B 5/008; G01B 3/008;
G01B 11/2518; G01B 21/042; G01B
11/25; G05B 2219/37274; B82Y 35/00;
G01Q 70/06; G01Q 10/06; Y10S
977/849; Y10S 977/867; Y10S 977/874
USPC ....... 382/154; 703/1, 11, 602, 633, 634, 641
See application file for complete search history.

(56) References Cited

U.S. PATENT DOCUMENTS

| | | | | |
|---|---|---|---|---|
| 5,042,305 | A * | 8/1991 | Takishita | B82Y 15/00 73/625 |
| 5,107,844 | A * | 4/1992 | Kami | A61B 8/12 600/446 |
| 5,476,010 | A * | 12/1995 | Fleming | G01N 29/0609 340/980 |
| 5,557,456 | A * | 9/1996 | Garner | G02B 21/367 359/383 |
| 6,009,755 | A * | 1/2000 | Manome | G01N 29/0609 73/602 |
| 6,122,967 | A * | 9/2000 | Sword | G01N 29/041 73/621 |
| 6,611,617 | B1 * | 8/2003 | Crampton | G01B 11/2518 356/614 |
| 7,181,970 | B2 | 2/2007 | Haase et al. | |
| 7,689,032 | B2 | 3/2010 | Strassenburg-Kleciak | |
| 8,087,298 | B1 * | 1/2012 | DiMambro | G01N 29/226 73/629 |
| 8,171,771 | B2 | 5/2012 | Hain et al. | |
| 8,205,500 | B2 | 6/2012 | Wu et al. | |
| 8,371,171 | B2 | 2/2013 | Isobe et al. | |
| 8,413,515 | B2 * | 4/2013 | Isobe | G01N 29/221 73/602 |
| 8,605,983 | B2 * | 12/2013 | Weston | G01B 11/007 348/48 |
| 2002/0062077 | A1 | 5/2002 | Emmenegger et al. | |
| 2002/0102023 | A1 * | 8/2002 | Yamauchi | G06F 19/3437 382/199 |
| 2004/0107080 | A1 * | 6/2004 | Deichmann | A61F 11/08 703/6 |
| 2005/0090743 | A1 * | 4/2005 | Kawashima | A61B 5/06 600/443 |
| 2005/0166413 | A1 * | 8/2005 | Crampton | B25J 13/088 33/503 |
| 2005/0256402 | A1 * | 11/2005 | Kawashima | A61B 8/12 600/437 |
| 2006/0288756 | A1 * | 12/2006 | De Meurechy | G01N 17/006 73/1.01 |
| 2009/0235749 | A1 * | 9/2009 | Ehara | G01N 29/07 73/622 |
| 2010/0018069 | A1 * | 1/2010 | Ould | G01B 21/042 33/503 |
| 2010/0149525 | A1 * | 6/2010 | Lau | G01B 11/002 356/139.03 |
| 2011/0000299 | A1 * | 1/2011 | Isobe | G01N 29/221 73/625 |
| 2011/0107270 | A1 | 5/2011 | Wang et al. | |
| 2011/0141270 | A1 | 6/2011 | Miyake | |
| 2011/0270562 | A1 * | 11/2011 | Ito | G01B 11/25 702/94 |
| 2012/0053462 | A1 * | 3/2012 | Kim | A61B 8/0858 600/443 |
| 2013/0319071 | A1 * | 12/2013 | Vodnick | G01B 21/047 73/1.08 |
| 2014/0268108 | A1 * | 9/2014 | Grau | G01B 5/008 356/72 |
| 2015/0000410 | A1 * | 1/2015 | Grimard | G01N 29/265 73/634 |
| 2015/0316513 | A1 * | 11/2015 | Grimard | G01N 29/4463 702/103 |

FOREIGN PATENT DOCUMENTS

| | | |
|---|---|---|
| EP | 1815936 B1 | 11/2009 |
| EP | 2325625 A1 | 5/2011 |

* cited by examiner

METHOD AND APPARATUS FOR SCANNING AN OBJECT

TECHNICAL FIELD

The present disclosure relates to the field of non-destructive testing. More specifically, the present disclosure relates to a method and an apparatus for scanning an object.

BACKGROUND

Mechanical scanning of regularly shaped objects, such as for example flat or slightly curved objects, is well documented and widely used. A structure of an object is typically mapped by software using a grid, for example a rectangular grid, in which a length and a width of each rectangular pixel of the grid is identical. The grid is typically aligned with main axes of a scanner, designated axes x and y, and a scanning motion is obtained by moving a probe, for example an ultrasonic probe, along one axis or along a combination of axes (for instance x) and repeated after indexing along a perpendicular direction by moving one or a set of axes (for instance y), while maintaining a distance between the probe and the structure surface. Some systems use a plurality of such probes.

Trigger signals are generated to initiate ultrasonic pulse generation and data acquisition when the probe reaches positions set by the grid. Encoder signals of the main scanning axis (for example x) are monitored by an encoder counter that generates the trigger signals at required probe positions. The probe is indexed in a perpendicular direction by a distance dictated by dimensions of the pixels on the grid at the end of the scanning motion. The scanning motion is then repeated for a new index position.

Three-dimensional (3D) ultrasonic scanning has been achieved in the past based on input of 3D computer-aided design (CAD) files. Motion of a 3D probe is obtained by inversed kinematics allowing moving a probe at constant distance and orientation with regards to a single surface of a scanned object. A virtual axis, composed of a motion control input/output, amplifier drive, motor and encoder, is calibrated to move synchronously with the 3D probe motion as the 3D probe follows a scanned surface. The encoder of this virtual axis represents movements along a single surface and is monitored during 3D movements of real axes. Trigger pulses are generated at equal distances traveled by the encoder of the virtual axes, providing a way to generate trigger pulses representing a travel over a complex surface.

Transmission scanning is achieved by adding a second, receiving probe facing an exit surface, opposite from a first emitting probe facing the scanned surface. The receiving probe follows the emitting probe, which is controlled in three dimensions as expressed hereinabove. A constant orientation and distance is maintained between the emitting and receiving probes. In controlling movement of the emitting and receiving probes, no consideration is given to the exit surface.

Currently available techniques are not well-suited for scanning of complex shapes, especially for those presenting curved surfaces defined in a 3D space. Needs exist for scanning complex objects, in particular for non-destructive testing purposes.

Therefore, there is a need for techniques that enable efficient scanning of complex shapes.

SUMMARY

According to the present disclosure, there is provided a method of scanning an object. Two virtual, orthogonal axes are positioned on a surface of the object. A scanning path of a probe is controlled as a function of the two virtual, orthogonal axes.

According to the present disclosure, there is also provided an apparatus for scanning an object. The apparatus comprises a movable support, a probe and a controller. The probe is mounted on the movable support. The controller is operably connected to the movable support and to the probe. The controller is configured to calculate a position of two virtual, orthogonal axes on a surface of the object and to control a scanning path of the probe as a function of the two virtual, orthogonal axes.

The foregoing and other features will become more apparent upon reading of the following non-restrictive description of illustrative embodiments thereof, given by way of example only with reference to the accompanying drawings.

BRIEF DESCRIPTION OF THE DRAWINGS

Embodiments of the disclosure will be described by way of example only with reference to the accompanying drawings, in which.

DETAILED DESCRIPTION

Figure 1:
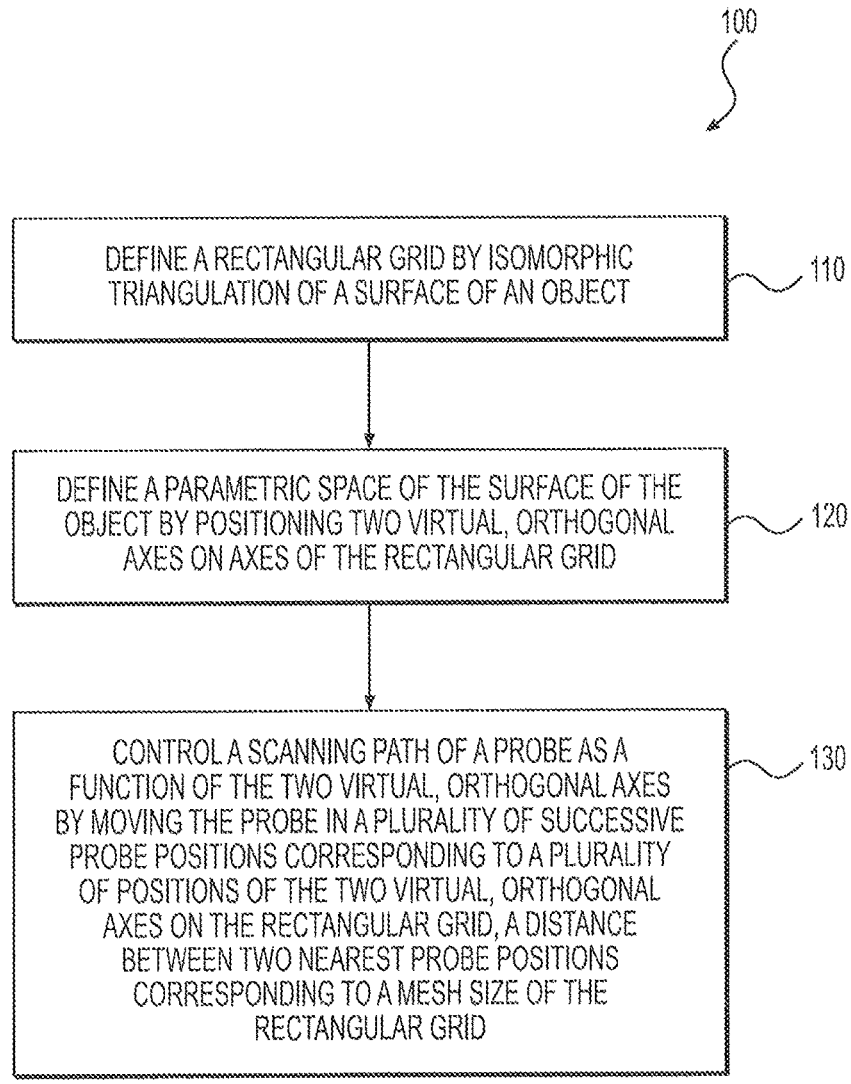
FIG. 1 is a flowchart showing operations for scanning an object.

Like numerals represent like features on the various drawings.

Various aspects of the present disclosure generally address one or more of the problems of scanning of complex shapes, including without limitations curved shapes and those shapes presenting surfaces defined in a three-dimensional (3D) space.

The following terminology is used throughout the present disclosure:

Probe: a physical device capable of sending and/or receiving a signal towards an object under test.

Scanning path: a series of consecutive positions of a scanner probe.

Pulse: a brief signal emitted by a probe.

Isomorphic triangulation: mapping of a surface into a plurality of adjoining triangles using a constant arrangement of triangles of variable dimension and angles, in which the number of adjacent triangles attached to each vertex enclosed within the boundaries of the surface remains constant throughout the whole surface of an object.

Rectangular grid: tessellation of a surface into a rectangular mosaic.

Mesh size: smallest length or depth of a rectangle in a rectangular grid.

Parametric space: mathematical representation of a surface, for example as a rectangular grid.

Virtual axis: mathematical representation of an axis on a parametric space, for example axes of a rectangular grid.

Contour: broad perimeter fully enclosing a scanned object.

Pulse-echo mode: signal acquisition mode of a probe in which a pulse is emitted by the probe and a reflected signal is acquired by the same probe.

Transmission mode: signal acquisition mode in which a pulse is emitted by an emitting probe and acquired by a receiving probe after transmission through an object.

Entry surface: surface of an object receiving a pulse from a probe.

Exit surface: surface of an object from which a pulse, received at an entry surface, exits after transiting through the object.

Couplant material: a medium present between a probe and a surface of a scanned object, including without limitation water, air, or another fluid.

Controller: a processor, a computer, a combination of processors and/or computers, possibly including a memory, an interface, and similar components, the controller may be hardwired for carrying a function or may comprise programmable code for carrying a function.

Movable support: mechanical device capable of moving under control of a controller while supporting a probe or a plurality of probes.

Command: a control signal sent from a first component to a second component for initiating an action of the second component.

Multi-axis: a mechanical device capable of moving in translation or in rotation along more than one axis.

Phased array of probes: a plurality of probes grouped in a manner allowing production of a predetermined pattern of pulses.

Non-destructive testing: a material evaluation technique that does not cause damage to an object under test.

C-Scan image: an image constructed by retrieving information from ultrasonic signals resulting from ultrasonic scanning of an object, the ultrasonic signals being recorded at each position on a rectangular grid applied on a scanned object.

In an embodiment, the present disclosure presents a method of scanning an object. Without limitation, the object may comprise one or more curved surfaces. Two virtual, orthogonal axes are positioned on a surface of the object. A scanning path of a probe is controlled as a function of the two virtual, orthogonal axes.

In another embodiment, the present disclosure presents an apparatus for scanning an object. The apparatus comprises a movable support, a probe and a controller. The probe is mounted on the movable support. The controller is operably connected to the movable support and to the probe. The controller is configured to calculate a position of two virtual, orthogonal axes on a surface of the object and to control a scanning path of the probe as a function of the two virtual, orthogonal axes.

The disclosed method and apparatus can be used for various applications, including without limitation for non-destructive testing purposes.

Referring now to the drawings, FIG. 1 is a flowchart showing operations for scanning an object. In FIG. 1, a sequence 100 comprises a plurality of operations that may be executed in variable order, some of the operations possibly being executed concurrently, some of the operations being optional. Operation 110 comprises defining a rectangular grid by isomorphic triangulation of a surface of an object. A parametric space of the surface of the object is defined in operation 120 by positioning two virtual, orthogonal axes on axes of the rectangular grid. At operation 130, a scanning path of a probe is controlled as a function of the two virtual, orthogonal axes. Without limitation, the probe may be an ultrasonic probe including for example an immersible probe or an air coupled probe, an eddy current probe, a laser probe, a hybrid probe, and the like. Operation 130 involves moving the probe along a scanning path that can include a plurality of successive probe positions corresponding to a plurality of positions of the two virtual, orthogonal axes on the rectangular grid. In a variant, a distance between two nearest probe positions corresponds to a mesh size of the rectangular grid.

The parametric space can be based on surfaces extracted from a computer aided design (CAD) file representing the object. Alternatively, a curvature and a contour of a surface of the object can be manually defined by an operator, following which the rectangular grid can be defined within the contour of the object.

The probe can operate in pulse echo-mode or in transmission mode. In the pulse-echo mode, the probe emits pulses that are reflected on the surface of the objet and the same probe detects an echoic signal. In transmission mode, the probe is an emitting probe facing an entry surface of the object and a second, receiving probe faces an exit surface of the object, moving in synchrony with the scanning path of the emitting probe to detect a signal resulting from transmission of an emitted pulse through the object. Of course, either the echoic signal or the transmitted signal both result from an originally emitted pulse. The echoic or transmitted signal is distorted when compared to the originally emitted pulse. Analysis of the amplitude, time of flight and other characteristics of the echoic or transmitted probe can provide an understanding of characteristics of the object, including beneath its surface.

Instead of moving a single probe operating in pulse-echo mode or a single pair comprising a single emitting probe paired with a single receiving probe, the sequence 100 may comprise moving a phased array of pulse-echo probes, or moving synchronized phased arrays of emitting and receiving probes along the scanning path.

Figure 2:
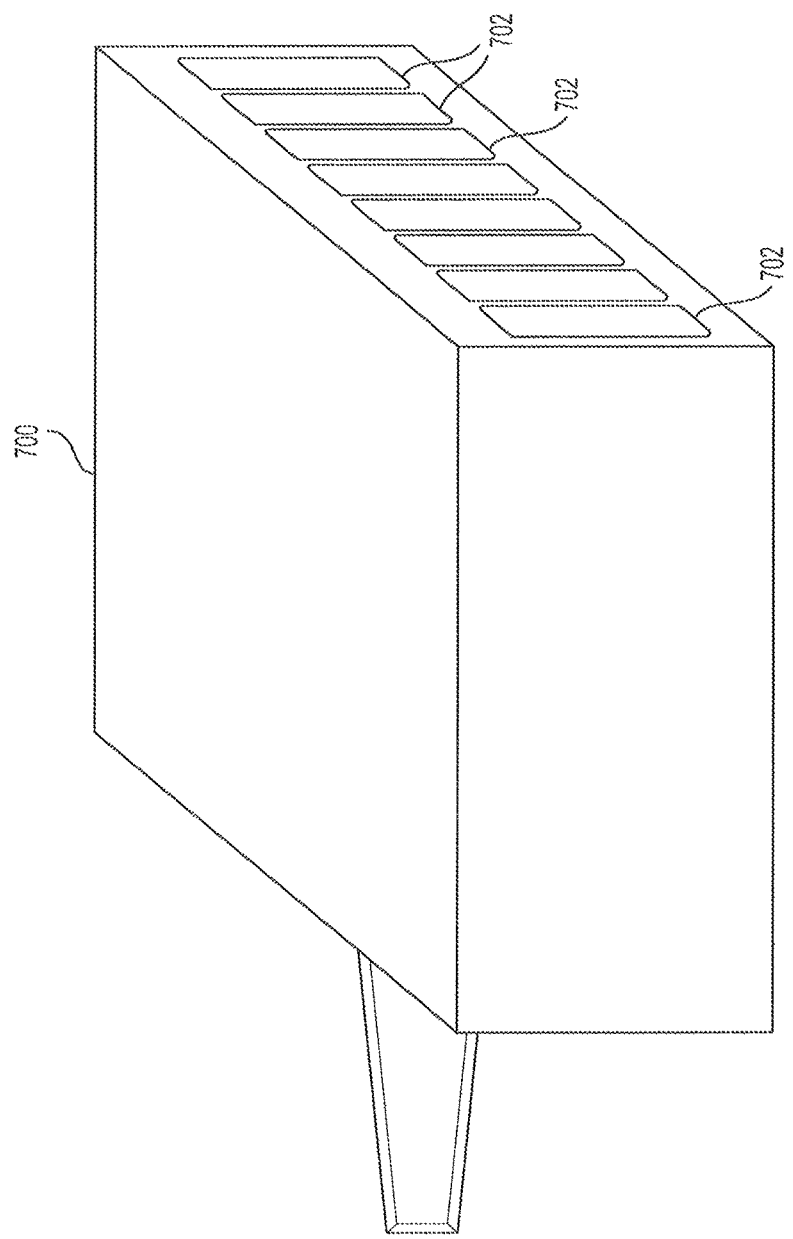
FIG. 2 is a schematic view of a phased array probe.
Figure 3:
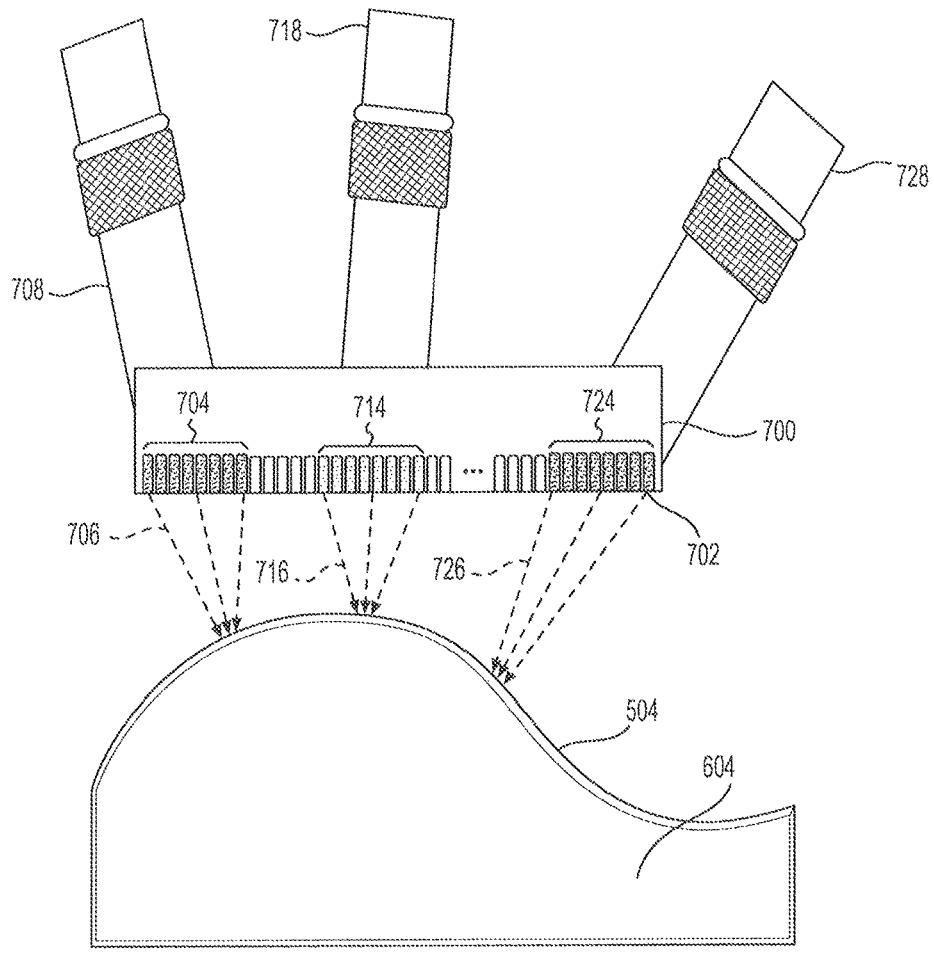
FIG. 3 is a schematic view of the phased array probe of FIG. 2 combining some of its array elements to form three (3) equivalent probes.

FIG. 2 is a schematic view of a phased array probe. FIG. 3 is a schematic view of the phased array probe of FIG. 2 combining some of its array elements to form three (3) equivalent probes. Referring at once to FIGS. 2 and 3, a phased array probe 700 faces a surface 504 of an object 604. In a first variant, array elements 702 are controlled in a manner that combines their aim to steer or focus a beam 706 impinging on the surface 504. Steering of the beam 706 can comprise focusing ultrasounds at a desired depth under the surface 504 of the object 604 or at a desired angle on the surface 504. The phased array probe 700 can focus on each position of the rectangular grid, one point at a time. In this case, the phased array probe 700 is used and operated as a single virtual probe 708. In a second variant, subsets 704, 714 and 724 of the array elements 702 are grouped, for example in groups of eight (8) elements, to form distinct virtual probes 708, 718 and 728 that steer beams 706, 716 and 726 to impinge on various points of the surface 504. For a given position of the phase array probe 700, through electronic control of the array elements 702 to adjust a focal law for each element group 704, 714 and 724 based on the curvature of the surface 504, more than one point of the surface 504 are concurrently covered.

Figure 4:
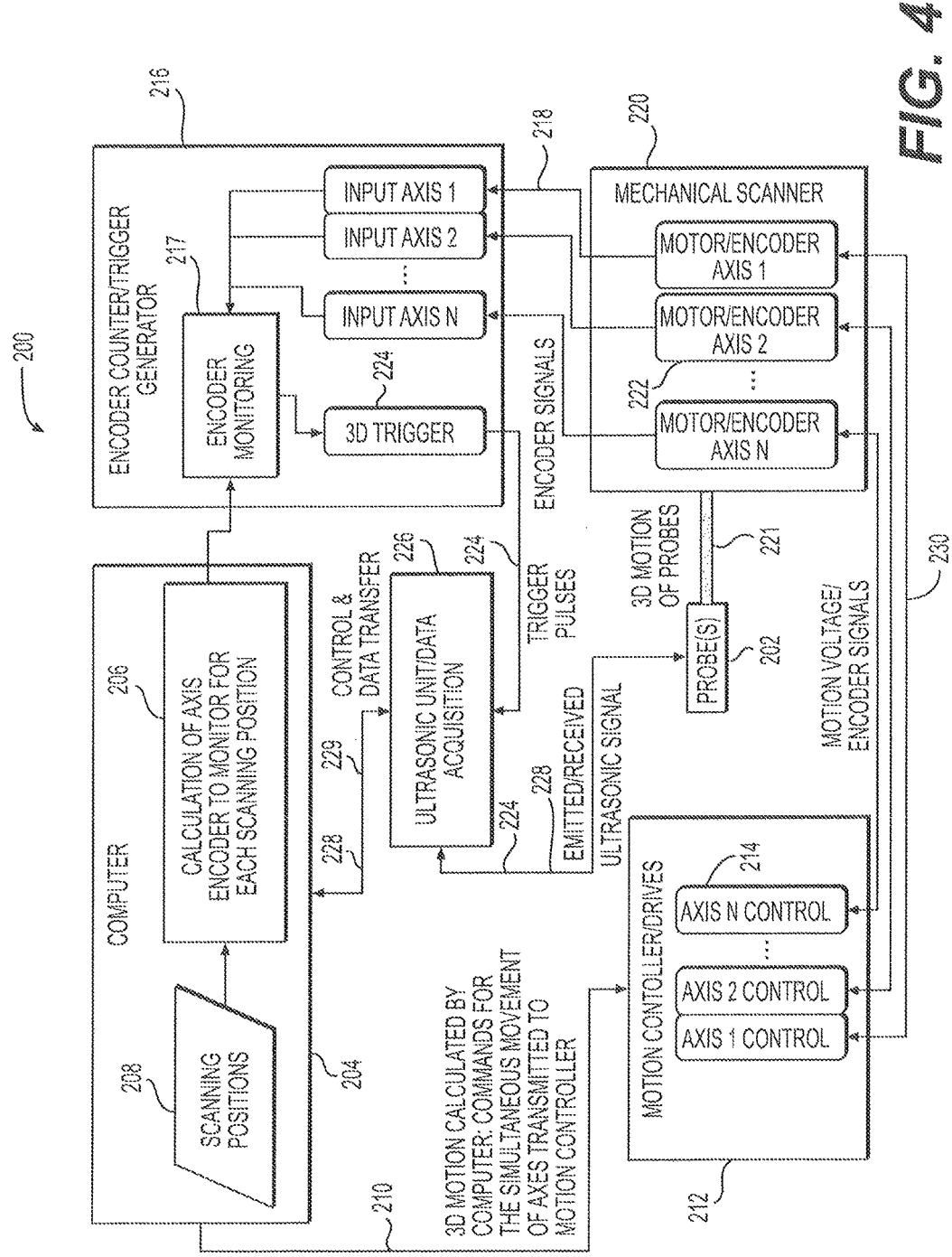
FIG. 4 is a block diagram of a scanning apparatus representing an information flow within the apparatus.

FIG. 4 is a block diagram of a scanning apparatus representing an information flow within the apparatus. An apparatus 200 for scanning an object comprises a plurality of components, some of which are optional. The various components of the apparatus 200 may be implemented as stand-alone modules or can alternatively be combined in one or more modules, the modules being realized as printed circuit boards, electronic circuits, processors, computers, and like devices. The apparatus 200 as shown on FIG. 4 is for illustration purposes. The apparatus 200 comprises a movable support (shown on later Figures), one or more probes 202, for example an ultrasonic probe, mounted on the movable support, and a controller. The controller comprises a computer 204, an encoder monitoring module 216 and an ultrasonic data acquisition unit 226. The controller is operably connected to the movable support and to the probe 202. The controller is configured to calculate position information 211 related to two virtual, orthogonal axes on the surface 504 of an object 604 to be scanned and to control a scanning path of the probe 202 as a function of the two virtual, orthogonal axes. The computer 204 has module 206 that calculates a position of the two virtual, orthogonal axes on the surface of the object as a function of known scanning positions 208 that may be obtained, for example, from a CAD file or from a prior analysis of the object. The computer 204 provides positioning commands 210 to a motion controller 212, which converts them to a voltage applied to motors, for example servo motors (not shown), for continuously moving the movable support, and the probe 202, along consecutive positions of the scanning path on the surface 504 of the object 604. The computer stores control parameters 229 provided to the ultrasonic data acquisition unit 226. Generally, the computer 204 comprises executable code to perform or to control the various operations of the sequence 100 of FIG. 1.

The encoder monitoring module 216 receives probe position information 218 from encoders 222 of a mechanical scanner 220 operably connected to the movable support. The encoder monitoring module 216 also receives the position information 211 related to the two virtual, orthogonal axes. The position information 211 is a function of positions of each individual axis of the apparatus 200 and comprises a combination of positions of all axes involved in the displacement of the probe 202. Within the encoder monitoring module 216, an encoder monitoring process 217 analyses the position information 211 related to the two virtual, orthogonal axes and the probe position information 218 to generate pulse commands 224 that are sent to the ultrasonic data acquisition unit 226.

A variant of the apparatus 200 using stepper motors (not shown) to move the movable support can be contemplated. With stepper motors, the probe position information 218 becomes unnecessary since the positioning commands 210 bring the movable support to a desired position directly, without a need for positional feedback. With stepper motors, each one of successive voltage pulses results in a predetermined advance of the movable support. A nearly continuous movement is obtained by generating a rapid train of pulses. A displacement amount of the movable support corresponding to each pulse being set by configuration of the apparatus 200, the encoder monitoring module 216 can therefore use the positioning commands 210 directly as a substitute for the position information 218.

Having received the pulse commands 224, the ultrasonic data acquisition unit 226 forwards the pulse commands 224 to the probe 202 that generate pulses from the pulse commands 224. The same probe or another probe 202 detects signals reflected by or transmitted through the object and forwards signal information 228 to the ultrasonic data acquisition unit 226. The ultrasonic data acquisition unit 226 then forwards the detected signal information 228 to the computer 204.

Having initiated a pulse sent by the probe 202 and having received and stored signal information 228 resulting from the probe, the computer 204 controls generation of a next pulse as the probe 202 passes at a desired location on the surface 504 of the object 604. After a pulse has been generated, the computer 204 determines when a next pulse is generated by selecting a physical axis to be monitored. This process can be illustrated by considering a simple case of a probe motion that involves movements of physical axes X and Y in a scanning path forming a circular motion of the probe around a scanned object, in a plane defined by the axes X and Y. The circumference of this circular scanning path defines a total linear displacement of the probe over 360 degrees in the plane. Assuming that a minimum inspection coverage requirement for the object impose generation of a pulse command every time the probe moves by one (1) mm along this circumference, based on an encoder signal of one of axes X or Y, a decision is made for each upcoming position to determine whether the position of the X or Y axis is to be monitored. This determines when to generate a pulse command. A linear movement of 1 mm along the circumference of the circular scanning path involves a different amplitude of movement for the X and Y axes. In some areas, there is very little movement along the X axis and most of the 1 mm movement takes place on the Y axis. The opposite occurs in other areas of the circular scanning path. It may be observed that monitoring a single one of axes X and Y does not provide sufficient information to define a circle and, in some cases, the movement along that single monitored axis can be too small or null. Consequently, a new axis is selected at each new upcoming probe position.

To determine when the next pulse is generated, after having selected the physical axis to be monitored, the module 206 calculates a next position information 211 of the two virtual, orthogonal axes on the surface of the object. Of course, a variant in which successive values of position information 211 are calculated at once is within the scope of the present disclosure. For example, the module 206 can calculate at once a full displacement along a given virtual axis, for a fixed position on another virtual axis. A sequence described herein, in which one value of the position information 211 is calculated before each pulse generation, is for illustration purposes and does not limit the present disclosure. The encoder monitoring process 217 uses this next position information 211 of the two virtual, orthogonal axes and uses updated probe position information 218 to generate a new pulse command 224 forwarded toward the probe 202. A series of consecutive positions of the two virtual, orthogonal axes forms the scanning path of the probe 202.

In a variant, available positions of the two virtual, orthogonal axes on the surface of the object can be constrained to map on a mesh of a rectangular grid defined by isomorphic triangulation of the surface of the object. In the same or other variant, a distance between two nearest positions of the pairs of virtual, orthogonal axes on the surface of the object correspond to a maximum desired distance between scanned locations on the object.

Regardless, the computer 204 may create an image (shown on a later Figure) of the object based on an analysis of a series of detected signal information 228. The image can be stored in memory (not shown) or forwarded to a display (not shown). The image can be used for example to detect flaws of the object that may not be visible from its surface.

The motion controller 212 of the movable support receives the positioning commands 210 for moving the probe (or probes) 202. In turn, the encoders 222 detect movements 221 of the probe 202 and provide the probe position information 218 to the encoder monitoring module 216. Because the movable support may be a multi-axis movable support, the motion controller 212 may comprise a plurality of axis controllers 214 and the mechanical scanner 220 may comprise a plurality of encoders 222. Each encoder 222 tracks a position of a motor axis. The axis controllers 214 and the encoder monitoring module 216 both monitor signals from the encoders 222. The axis controllers 214 use positional information to adjust voltages applied to motor axes in order to control the axis displacement speed and smoothness and further to minimize differences between desired and attained positions during and at the end of a displacement event.

The positioning commands 210 may comprise a plurality of commands for moving the multi-axis movable support about a plurality of mechanical axes (shown on later Figures) and the encoders 222 of the mechanical scanner 220 may detect movements of the probe 202 about the plurality of mechanical axes. Consequently, the probe position information 218 may comprise information about the position of the probe 202 in the plurality of mechanical axes.

Motor voltage and encoder signals are exchanged 230 between the plurality of axis controllers 214 and corresponding encoders 222, providing feedback in order to ensure smooth motion of the probe 202. In particular, voltage applied to the various motors is impacted by information received from the encoders 222.

The probes 202 may comprise an emitting probe positionable facing an entry surface of an object being scanned and a receiving probe positionable facing an exit surface of the object. When such a pair of probes 202 is used, the controller provides positioning commands 210 and acts upon probe position information 218 of both probes to control a synchronized scanning path of the emitting probe and of the receiving probe. In a variant, relative positions of the emitting and receiving probes may be mechanically fixed, in which case synchronized motion of the probes is inherently obtained. A variant showing an emitting probe and a receiving probe is shown on a later Figure.

In another variant, the phased array 700 forming a plurality of virtual probes 708, 718 and 728 can be mounted on the movable support and configured to concurrently inspect a plurality of positions of corresponding pairs of virtual, orthogonal axes on the surface of the object. The module 206 of the computer 204 calculates positions of the pairs of virtual, orthogonal axes on the surface of the object as a function of known scanning positions 208 of each of the virtual probes 708, 718 and 728 of the phased array 700. The encoder monitoring process 217 analyses the information 211 related to each pair of virtual, orthogonal axes and the probe position information 218 of each corresponding virtual probes 708, 718 and 728 to generate pulse commands 224 addressed to each respective virtual probes 708, 718 and 728.

Various embodiments of the method and apparatus for scanning an object, as disclosed herein, may be envisioned. The following paragraphs present non-limiting features that may be present in some embodiments and not in other embodiments.

The scanning apparatus and method for disclosed herein can be used for ultrasonic scanning of complex shapes presenting curved surfaces defined in a 3D space. The method and apparatus allow inspection of a complex shaped structure, typically a composite material shaped for aerospace applications, using one or multiple ultrasonic probes moved using a combination of linear and rotational mechanical axes. The ultrasonic probes can operate in pulse-echo or through-transmission mode. By respecting a maximum distance between each probe position along the structure surface, a C-Scan image of the structure can be produced based on data resulting from reflection or transmission of ultrasonic pulses. This process involves mapping a 3D surface of the object on a rectangular grid defined in a parametric space, where each adjacent elements of the 3D surface of the object forming a mesh of the grid are separated by a maximum distance corresponding to a desired inspection coverage and overlap. In this manner, a maximum distance between points of entry and exit of the ultrasonic waves along the surface can be controlled by defining a mesh size of the grid.

Therefore, mapping of surfaces of a 3D structure into a parameterized space defined by two (2) virtual orthogonal axes can define a synchronized movement of multiple mechanical axes supporting one or more probes along the surface. This can be used for inspection from a single side, in a pulse-echo mode, or from both sides of the structure, in a through-transmission mode. Controlled movement of the probes along virtual axes defined in a parametric space can adopt a jogging mode, follow absolute parametric positions, form an automated scan, and the like. Trigger pulses can be generated at equidistant positions of a parametric axis defined on a curved surface, using mechanical axes of the scanner without the need for an additional motor/drive. C-Scan images can be generated at a controlled resolution. A decision process can select a proper axis or axes that need to be monitored to generate equidistant trigger pulses.

The disclosed method and apparatus for 3D ultrasonic scanning can be applied to a pulse-echo inspection by following a single structure surface or, in transmission by following two opposing surfaces of a structure. Mapping of the surfaces can be achieved manually if the structure can be defined as the repetition of a curve along another curve, as in the case of a swept surface, for example a revolution or extrusion surface. Mapping of the surfaces can alternatively be based on a CAD drawing. The former case is referred to as "2.5D" scanning or "contour following scanning", while the latter case is referred to as "3D scanning".

In the case of manual surface mapping (2.5D), the mapping applies to contour following scanning and comprises a definition of the external surface that needs to be covered by the ultrasonic inspection using an ultrasonic probe. A curvature of the surface is defined by positioning the probe in front of the surface contour and by adjusting the orientation of the ultrasonic probe until the ultrasonic echo returning from the surface of the material is optimized. This happens when the ultrasonic signal impinges perpendicularly on the surface. Using the sound velocity in a medium between the probe and the surface, for example in water, this gives a position and orientation of a point of the surface within limits of the ultrasonic scanner. This operation is repeated at different probe positions until a sufficient number of points have been defined to represent the curvature of the structure. In the case of a curve that is repeated cyclically on the object, coverage of a single repeatable pattern is sufficient. This operation is performed on the entry surface of the ultrasonic waves for pulse-echo scanning, and on both the entry and the exit surfaces of ultrasonic waves for transmission scanning. The points acquired on the surface are used in a process that generates a continuous contour within the limits defined by the acquired points using interpolation processes, for example a spline. Once the contour has been defined, the extent of the material along an axis perpendicular to the contour, for example on an extrusion axis, is defined to map the entire surface. The 2.5D surface is defined in a 2D parametric space with a set of orthogonal vectors $(\vec{u},\vec{v})$, where the curve obtained by ultrasonic measurements defines an axis of the parametric space (e.g. $\vec{u}$) and the curve along which the latter is repeated defines the second axis of the parametric space (e.g. $\vec{v}$).

Figure 5:
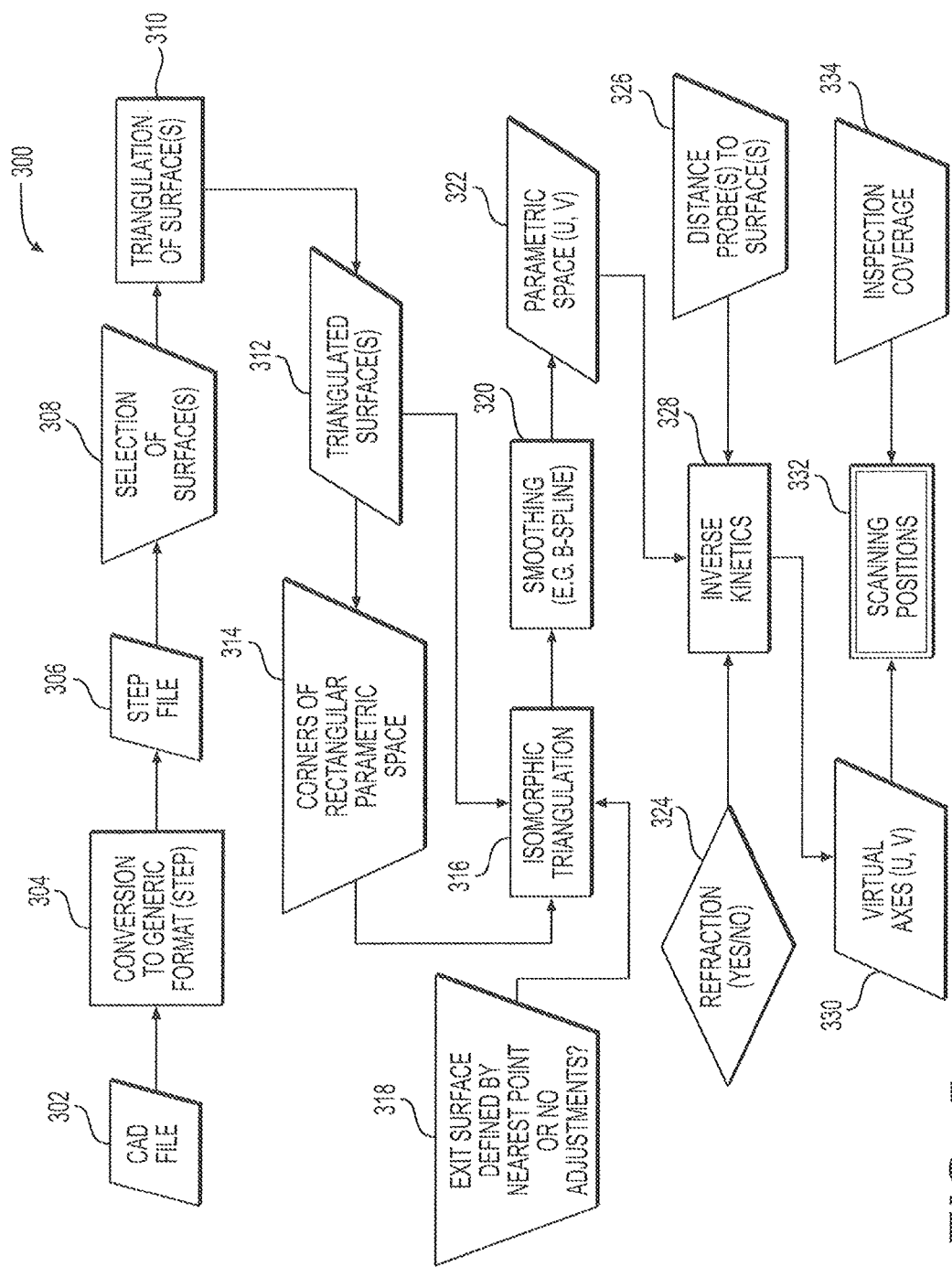
FIG. 5 is a flowchart showing operations for generating scanning positions from a computer assisted design file.

In the case of automated surface mapping (3D), a file including a CAD drawing representing the surfaces of the structure to be inspected can be used to map the surface for a 3D inspection. FIG. 5 is a flowchart showing operations for generating scanning positions from a computer assisted design file. A flowchart 300 comprises a plurality of operations that may be executed in variable order, some of the operations possibly being executed concurrently, some of the operations being optional. Software code implemented in the computer 204 is executable to perform or control performance of the operations of the flowchart 300. Surfaces from a CAD file 302 are converted 304 into a step file 306 prepared for 3D scanning software. Surfaces that need to be covered by the ultrasonic inspection, including a single surface for pulse-echo mode or two opposed, entry and exit surfaces for transmission scanning, are selected 308 and converted into a parametric space defined by the two orthogonal vectors $(\vec{u},\vec{v})$ using advanced triangulation processes. The objective of the triangulation is to create a rectangular parametric surface out of the 3D surface(s) of the structure. This allows to create C-Scan images from the acquired data, which is properly arranged on a rectangular grid.

A first triangulation 310 is performed on the imported surfaces, producing a triangulated surface file 312, from which four corners of a rectangular parametric surface, for example natural corners of the structure, are defined 314 based on the geometry of the surface to inspect. If transmission of ultrasound pulses is to be performed through the thickness of the structure, the corners of the entry and exit surface are defined in an orderly manner to associate the corners of each side for an optimal ultrasonic transmission. These corners define four boundaries of the parametric surfaces. A rectangular isomorphic triangulation is then calculated 316 on the output of the triangulation of the surfaces.

Figure 7:
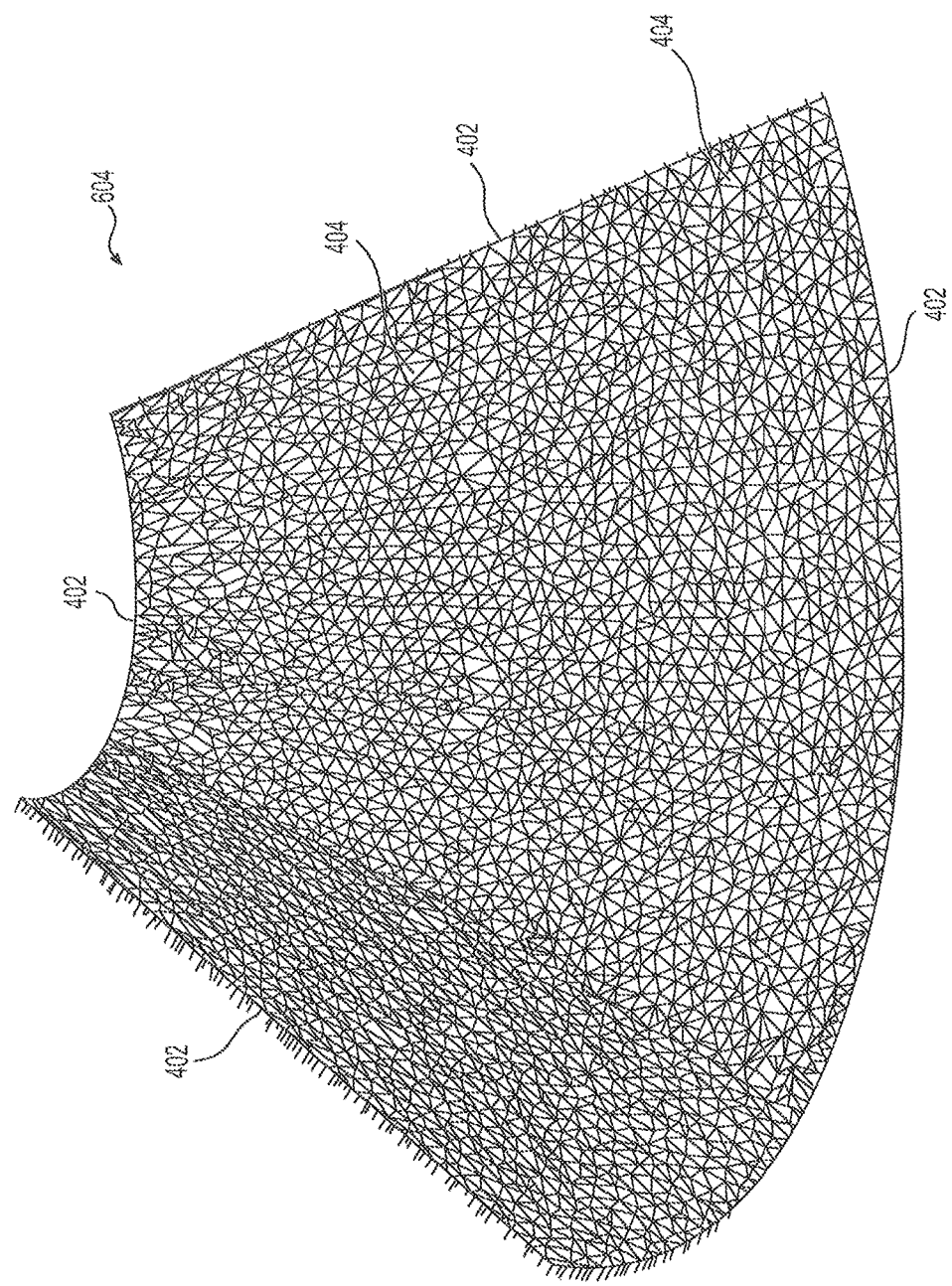
FIG. 7 is an example of a triangulation representing an imported surface.

FIG. 7 is an example of a triangulation representing an imported surface. An object 604 has been subjected to triangulation. Triangle vertices located on boundaries 402 of the surfaces of the object 604 define limits of the parametric surface. A position of each triangle vertex, such as 404, that is inside the boundaries of the surfaces is calculated in order to obtain smooth isoparametric curves.

Figure 8B:
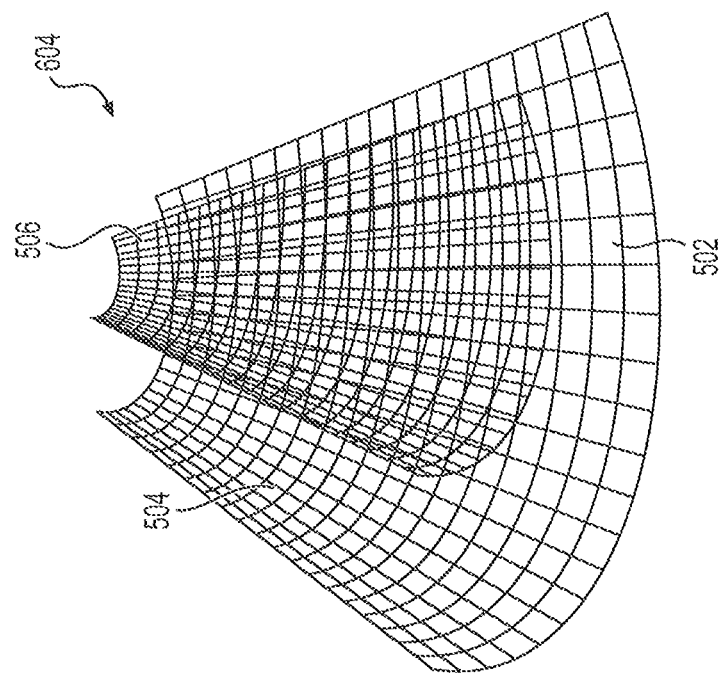
FIG. 8b is an example of a parametric space obtained from isomorphic triangulation of entry and exit surfaces.
Figure 8A:
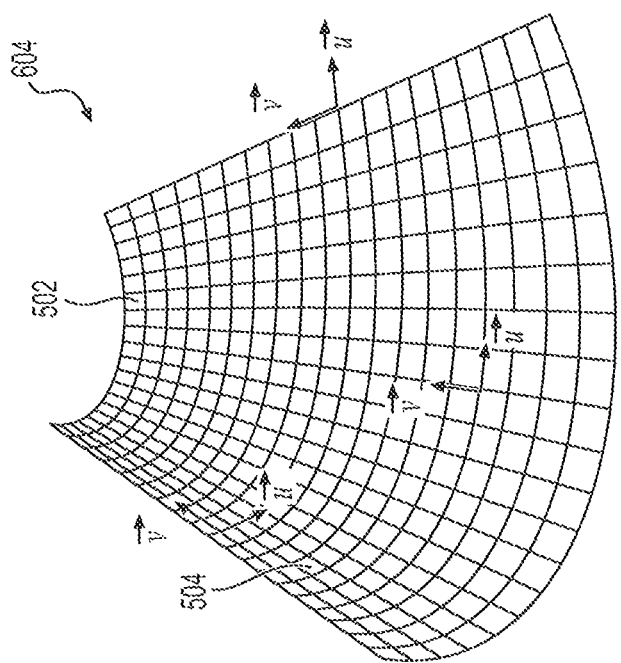
FIG. 8a is an example of a parametric space obtained from isomorphic triangulation of a single surface.

FIG. 8a is an example of a parametric space obtained from isomorphic triangulation of a single surface. FIG. 8b is an example of a parametric space obtained from isomorphic triangulation of entry and exit surfaces. Both FIGS. 8a and 8b show a mesh size 502 of a rectangular grid. While FIG. 8a only shows one surface 504, FIG. 8b shows that the surface 504 is an entry surface facing an exit surface 506. Examples of orthogonal vectors $(\vec{u},\vec{v})$ defining the parametric space are displayed on FIG. 8a; though not shown, the vectors $(\vec{u},\vec{v})$ are also definable on the entry and exit surfaces 504 and 506 of FIG. 8b.

Returning to FIG. 5, if transmission of ultrasound pulses is to be performed through the thickness of the structure of the object 604, three (3) options are available for the isomorphic triangulation 316. A selection point 318 provides one of these options. In a first case, for each point of the entry surface 504, an equivalent point is defined on the exit surface 506. This allows to fully cover both surfaces. This optimal coverage allows detection of flaws inside a volume enclosed between the entry and exit surfaces 504 and 506, as well as detection of bonding flaws between core material and bonded layers on the entry and exit surfaces 504 and 506. Alternatively, in a second case, for each point of the entry surface 504, a nearest point is found on the exit surface 506. This nearest point of the exit surface 506 is associated to that point of the entry surface 504. This option minimizes a distance travelled by the ultrasonic waves inside the structure of the object 604. In that case, the entry surface 504 is fully covered while the exit surface 506 is not necessarily fully covered. Detection can be made of bonding defects between a layer present at the entry surface 504 and core material of the object 604 while maintaining optimal ultrasound transmission through the volume of the object 604. A third case may be used in certain applications such as for inspection of honeycomb structures. In such a case, pulses are directed so that they impinge the structure in parallel to an alignment of a core of the honeycomb so that transmission is made through the material. This is achieved by associating points of the entry and exit surface so that they are aligned in parallel to the core arrangement. A variant may further impose a constant transmission angle.

A smoothing, or fit 320, performed for example as a B-Spline, is performed on the surface defined by the rectangular isomorphic triangulation to ensure a parametric surface that is sufficiently smooth to minimize jerking of the mechanical axes resulting from sudden changes in the local curvature of the parametric surface. This parameterization operation defines smooth axis displacements and an increased inspection speed. For two (2) surfaces, the parametric space is defined so that a given position of one surface is linked to a single position on the opposing surface. The output of this process is a parametric space 322 defined by the two orthogonal vectors $(\vec{u},\vec{v})$.

The probe 202 can move over a 3D space around a 2.5D surface or 3D a surface. For the case of the transmission mode, a selection 324 determines whether or not the effect of refraction is used to adjust angles of emitting and receiving probes.

Figure 6A:
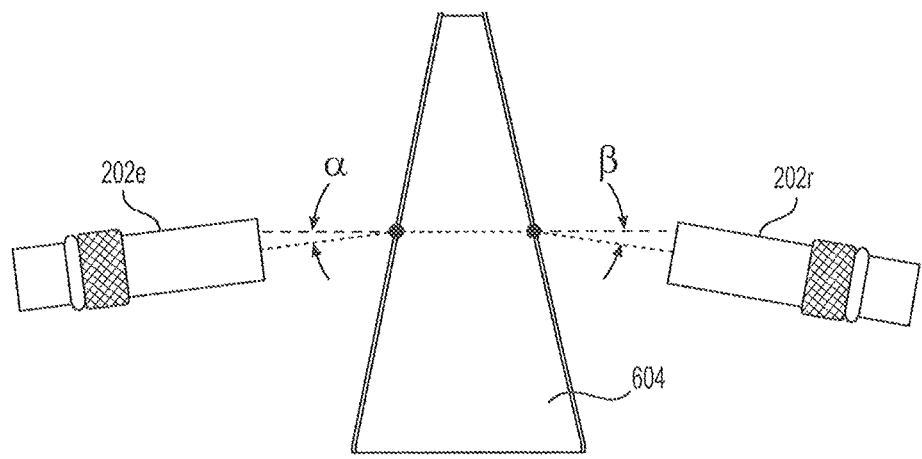
FIG. 6 is an illustration of transmission mode when the effect of refraction within an object is considered (A) or not (B)
Figure 6B:
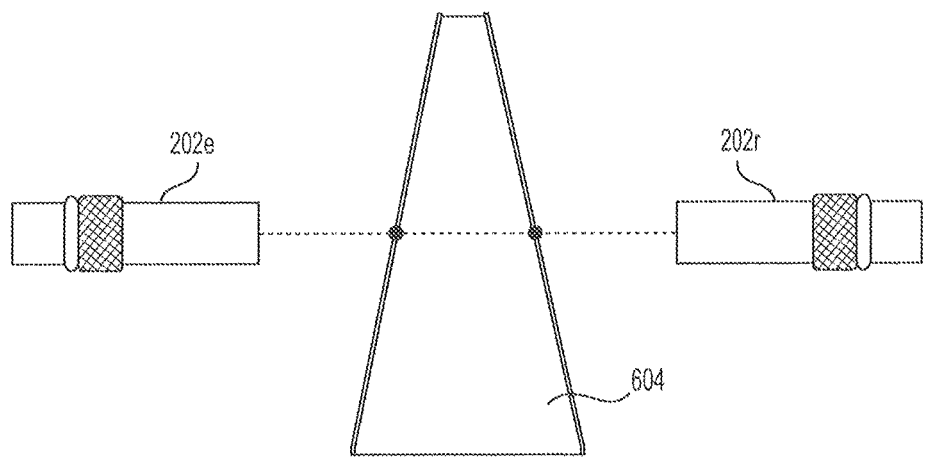

FIG. 6 is an illustration of transmission mode when the effect of refraction within an object is considered (A) or not (B). If the object 604 is known or assumed to be made of an isotropic material, the refraction effect is considered (case A in FIG. 6) and angles α, β of an emitting probe 202e and of a receiving probe 202r are adjusted in for aiming at corresponding entry and exit points on the object 604 while considering the refraction occurring within the object 604. If the refraction effect is not considered (case B in FIG. 6), the probes 202e and 202r are simply oriented to aim at each other and at and the entry and exit points on the object 604.

In another variant, an optimal angle for a probe used in pulse-echo mode can be set based on a desired refraction angle inside the object 604. In yet another variant, the receiving probe 202r can be replaced by a second emitting probe 202e, both emitting probes operating in pulse-echo mode, and optimal angles for each emitting probe can be determined.

A desired distance between the probe 202 and the surface of the object 604 is input by another user input 326. The sound velocity of the couplant material and the sound velocity of the object 604 are used to calculate the probe angle using Snell's law of refraction. For transmission scanning, a distance between the exit surface and the receiving probe is also input by another user input 326. Also in the case of transmission scanning using ultrasonic pulses, two options can be selected for determining probe angles. In a first option, sound velocity of the material forming the object 604 under test is used to calculate an angle of a probe on the entry surface (emitting probe 202e, shown on a later Figure) and of a probe on the exit surface (receiving probe 202r, also shown on a later Figure). The probe angles are chosen to allow entire coverage of the entry and exit surfaces, considering the wave refraction occurring at the interface between the couplant material and the entry surface of the object 604 under test, as well as at the interface between the couplant material and the exit surface of the object 604. In a second option, an angle used to align the emitting probe 202e and the receiving probe 202r is calculated so that it provides complete coverage of the entry and exit surface.

Inverse kinematics 328 define the scanning path that follows the surface of the object, for pulse-echo scanning, or follows the entry surface for the emitting probe 202e and the exit surface for the receiving probe 202r in transmission scanning. The inverse kinematics 328 apply the selection 324 in the case of transmission mode. The inverse kinematics 328 additionally apply the distance between the probe or probes and the surface or surfaces, determined at 326. These parameters and the parametric space 322 are used in the inverse kinematics 328 to define two orthogonal, virtual axes (U,V) 330. The virtual axes (U,V) 330 define simultaneous movements of the emitting and receiving probes 202e and 202r, in the case of transmission scanning, or defines the movement of the probe 202 for pulse-echo scanning. As mentioned hereinabove, pulse-echo can be performed on both sides of the object 604 using two (2) emitting probes, in which case the virtual axes (U,V) 330 define simultaneous movement of both emitting probes. Scanning positions 332 of the probe 202 follow the two orthogonal, virtual axes (U,V) 330 while applying at least a minimum inspection coverage parameter 334.

3D scanning is performed in the parametric space $(\vec{u}, \vec{v})$ by moving the mechanical axes simultaneously using the virtual axes (U,V). The resolution of the scan within axes (U,V) is defined in order to respect the minimum inspection coverage parameter 334 defining a maximum distance between two (2) adjacent scanned locations on the surface. Coordinates of the scanning positions 332 where data is desired to be recorded are defined in order to obtain a rectangular grid, providing a constant number of scanning points to record along the virtual axis U for all positions along the virtual axis V. The distance between 2 consecutive scanning positions 332 is not necessarily constant but is selected according to the maximum allowable distance.

Referring again to FIG. 4, emitting ultrasonic pulses and recording detected ultrasonic signal information 228 at the calculated scanning positions 332 involves generating trigger pulse commands 224 when the probe 202 reaches proper coordinates. This is achieved by monitoring the probe position information 218 related to one or multiple axes during scanning movement (e.g. along the U virtual axis). Since multiple mechanical axes are involved in the 3D motion of the probe 202, a process determines which encoder 222 is desired to be monitored during the probe 202 displacement. More than one axis can be monitored during a scanning movement but only one encoder 222 is used at a time. Thus, the encoder 222 that needs to be monitored can change between two adjacent scanning position 332 at a given index position during probe 202 movement along the scanning axis (e.g. along the U virtual axis). For each scanning position 332 where detected ultrasonic signal information 228 is desired to be recorded and where trigger pulses are desired to be generated, the probe position information 218 for the axis to be monitored is calculated and the encoder monitoring module 216 generates the pulse commands 224 at the proper scanning position 332. This is re-calculated for each index position (e.g. along the V virtual axis).

The computer 204 records detected ultrasonic signal information 228 based on the trigger pulse commands 224 and a C-Scan image is generated. Generally, each pulse generates one signal information element defining one pixel. Because each pixel of the scanned rectangular grid do not necessarily have the same dimensions, sizing tools (length, surface, etc.) applied to the C-Scan image are adapted to take true dimensions of each pixel into account.

Figure 9:
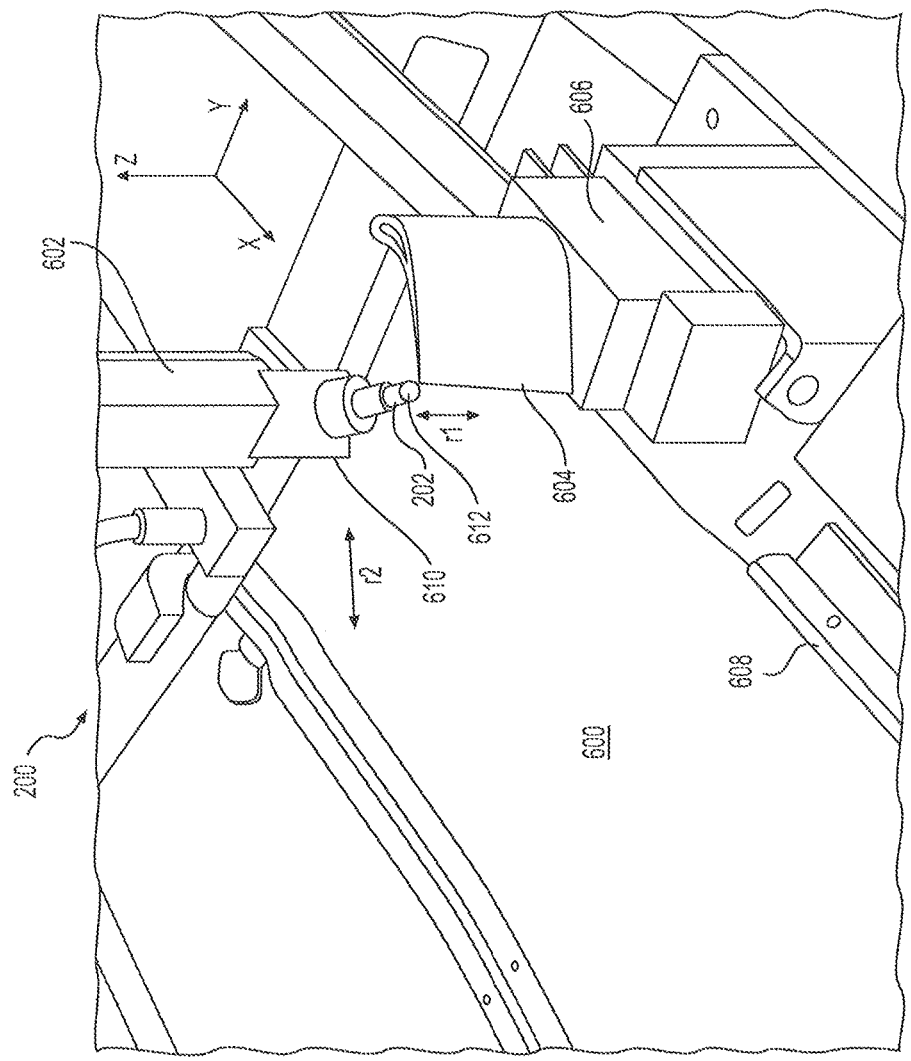
FIG. 9 is an example of an apparatus for scanning an object in pulse-echo mode.

FIG. 9 is an example of an apparatus for scanning an object in pulse-echo mode. A probe 202 operating in pulse-echo mode is mounted on a movable support 602 and faces a surface of the object 604 being scanned by the scanning apparatus 200. The object 604, the probe 202 and at least a lower extremity of the movable support 602 are immersed within a water basin 600. The object 604 is mounted on a support 606 that is itself fixedly mounted on a frame 608 of the water basin 600. Immersing the object 604 in water is one of many options. The scanning apparatus 200 can alternatively make use of a water jet or bubbler system to provide a local water column for wave propagation between the probe 202 and the object 604, of make use of air coupled probes 202 designed to emit and receive ultrasonic waves in air. In the example of FIG. 9, the probe 202 emits ultrasonic pulses that travel through water and impinge on the surface of the object 604. The pulses penetrate at least in part through a depth underneath the surface of the object 604 before being reflected and detected again by the probe 202. A reflection from an opposite surface of the object 604 may occur if nothing within the object material interferes with the transmission of the ultrasonic wave, or attenuates the transmitted ultrasonic waves down to an undetectable level, and if the wave hits the opposite surface at an angle that allows reflection back towards the probe 202. However, a flaw, for example a crack, a void, a porosity, an inclusion, a delamination, and the like, if present inside the object 604, may reflect of diffract the wave, depending on its composition, orientation and size, resulting in the probe 202 receiving a reflected or a diffracted wave or receiving no response to a given pulse. The movable support 602 moves longitudinally, laterally and vertically along axes x, y and z, and can thus reach various positions around the object 604. The probe 202 is held by a head 610 mounted on the movable support.

The head 610 rotates about a vertical axis r1 in order to allow facing a tip 612 of the probe in a normal axis with the surface of the object 604. The head 610 also rotates about a horizontal axis r2 in order to raise or lower the tip 612 of the probe 202 without moving the movable support 602. Considering at once FIGS. 4 and 9, the movable support 602 forms a five (5) axis support capable of moving up or down, longitudinally, laterally and, considering two rotational axes of the head 610, provides five (5) axes x, y, z, r1 and r2, under control of the positioning commands 210. The movements 221 of the probe 202 are detected over five (5) dimensions. Other configurations involving more or less degrees of freedom, including without limitation mutually perpendicular rotational axes, are also contemplated.

Figure 10:
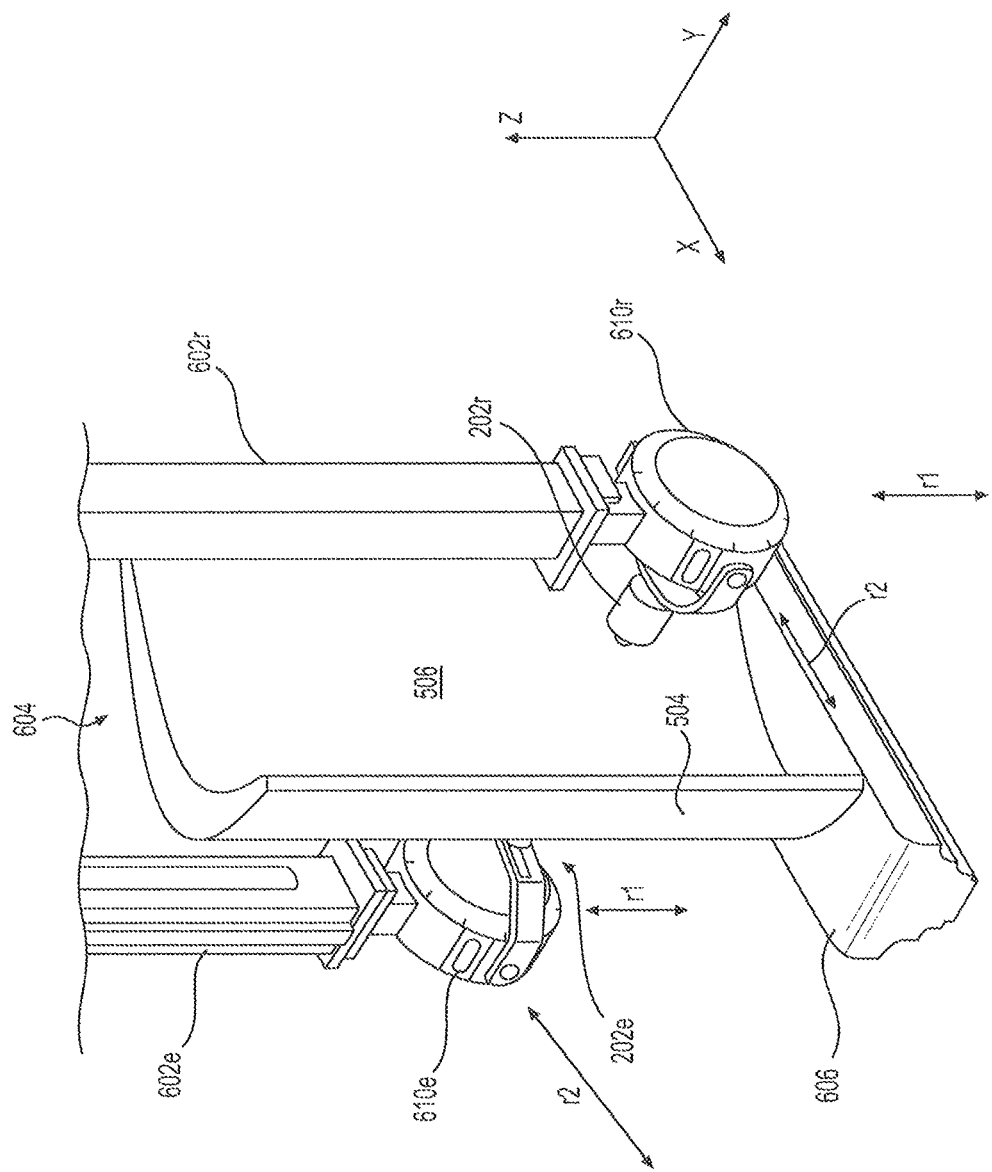
FIG. 10 is an example of an apparatus for scanning an object in through-transmission mode.

FIG. 10 is an example of an apparatus for scanning an object in through-transmission mode. An emitting probe 202e is supported by a movable support 602e having a head 610e. A receiving probe 202r is supported by a movable support 602r having a head 610r. In one embodiment, the two movable supports 602e and 602r and their respective heads 610e and 610r are synchronized so that the emitting probe 202e is normal to an entry surface 504 of the object 604 while the receiving probe 202r is co-aligned with an emission path of the emitting probe 202e, facing an exit surface 506 of the object 604. In another embodiment, angles of the emitting and receiving probes 202e and 202r with regards to the entry and exit surfaces of the object 604 can be set according to the selection 324 and to the principles introduced in the foregoing description of FIGS. 5 and 6. If the refraction effect is to be considered, the angle of the emitting probe 202e is adjusted based on the laws of refraction (Snell's law) in order to obtain a propagation path inside the object 604 that goes from the entry point to its corresponding exit point on the opposite surface. The same principle applies to the receiving probe 202e. The ultrasound wave traveling through the object 604 comes out at the exit point at an angle given by Snell's law. The receiving probe 202r points to the exit point at the angle calculated by the refraction law. In a variant, a synchronized but mechanically variable relationship between the two movable supports 602 and 602r may allow preserving a fixed distance between the emitting probe 202e and the entry surface of the object 604 while, at the same time, preserving a fixed distance between the receiving probe 202r and the exit surface of the object 604. A mechanically fixed relationship between the two movable supports 602 and 602r maintains a fixed distance between the emitting and receiving probes 202e and 202r. Amplitudes, shapes and frequencies of transmitted signals received by the receiving probe 202r are affected by the shape and thickness of the object 604, by what is present inside the object, for example flaws such as cracks, voids, porosity, inclusions, delaminations, and the like, such flaws impacting the ultrasonic waves in terms of attenuation, refraction, diffraction, loss of transmission due to total or partial reflection, and the like.

Because of varying shapes of the object 604 being scanned, the emitting probe 202e is not necessarily normal with the exit surface 506.

It may be observed that a definition of an entry or exit surface of the object 604 is not a feature of the object 604 but is to be considered in relation to a position of the emitting and receiving probes 202e and 202r. As the movable supports 602e and 602r rotate 180 degrees about a vertical axis of the object 604, the entry surface becomes and exit surface, and vice-versa.

Figure 11:
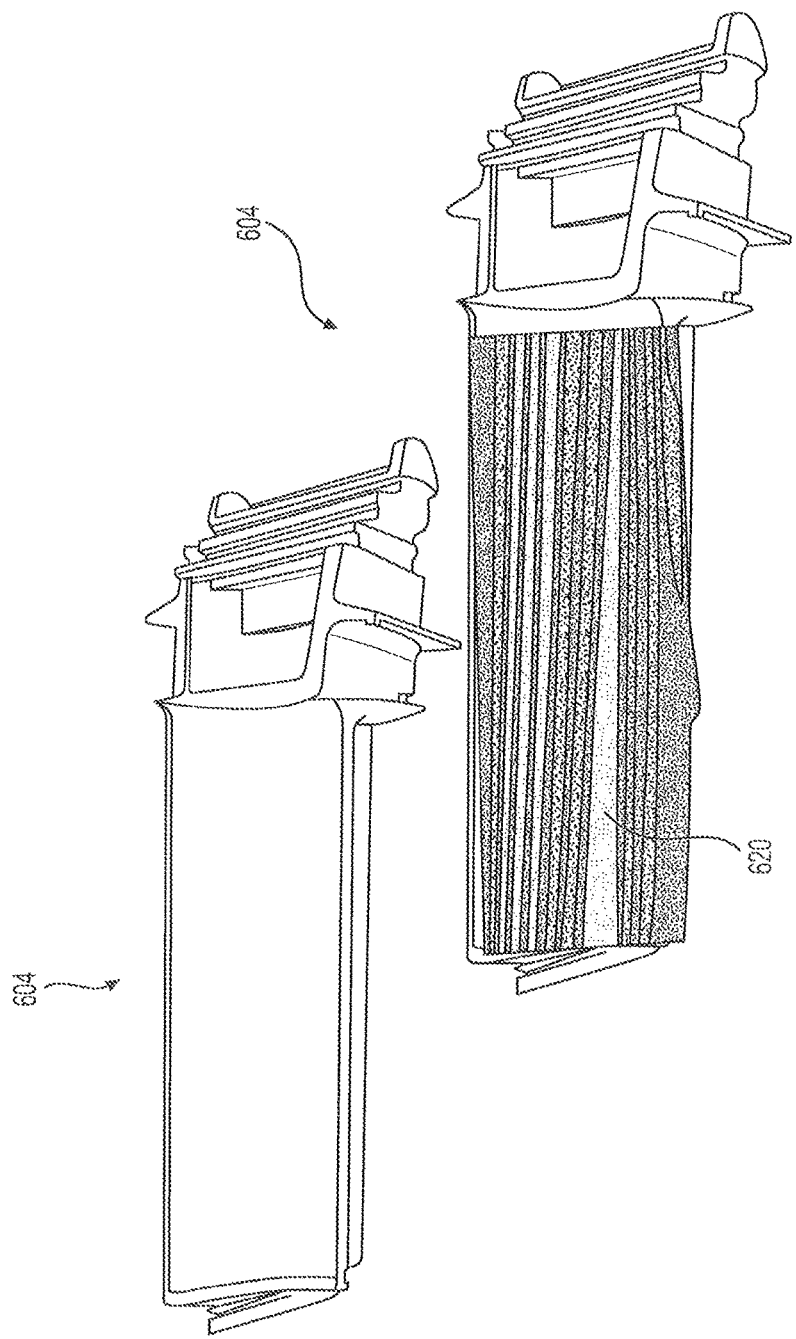
FIG. 11 is an image of a real-life object along with a scanning result of the real-life object.

FIG. 11 is an image of a real-life object along with a scanning result of the real-life object. The object 604 of preceding Figures is shown at the top of FIG. 11. The same object 604 is reproduced at the bottom of FIG. 11, an image 620 being superimposed on the object 604. Though FIG. 11 is two-dimensional, a C-Scan image can actually be projected on a 3D representation of the structure based on 3D surfaces defined in a CAD file. The image 620 has been created by the computer 204 based on the detected signal information 228 obtained in pulse-echo mode from one probe 202 having moved through the scanning path. Features of the image 620 represent depths of echoes returning from pulses having propagated underneath the entry surface of the object 604, revealing an inner structure of the object 604.

Those of ordinary skill in the art will realize that the description of the method and apparatus for scanning an object are illustrative only and are not intended to be in any way limiting. Other embodiments will readily suggest themselves to such persons with ordinary skill in the art having the benefit of the present disclosure. Furthermore, the disclosed method and apparatus may be customized to offer valuable solutions to existing needs and problems of scanning objects that have complex shapes.

In the interest of clarity, not all of the routine features of the implementations of the method and apparatus are shown and described. It will, of course, be appreciated that in the development of any such actual implementation of the method and apparatus, numerous implementation-specific decisions may need to be made in order to achieve the developer's specific goals, such as compliance with application-, system-, and business-related constraints, and that these specific goals will vary from one implementation to another and from one developer to another. Moreover, it will be appreciated that a development effort might be complex and time-consuming, but would nevertheless be a routine undertaking of engineering for those of ordinary skill in the field of non-destructive testing having the benefit of the present disclosure.

In accordance with the present disclosure, the components, process operations, and/or data structures described herein may be implemented using various types of operating systems, computing platforms, network devices, computer programs, and/or general purpose machines. In addition, those of ordinary skill in the art will recognize that devices of a less general purpose nature, such as hardwired devices, field programmable gate arrays (FPGAs), application specific integrated circuits (ASICs), or the like, may also be used. Where a method comprising a series of operations is implemented by a computer or a machine and those operations may be stored as a series of instructions readable by the machine, they may be stored on a tangible medium.

Systems and modules described herein may comprise software, firmware, hardware, or any combination(s) of software, firmware, or hardware suitable for the purposes described herein. Software and other modules may reside on servers, workstations, personal computers, computerized tablets, personal digital assistants (PDA), and other devices suitable for the purposes described herein. Software and other modules may be accessible via local memory, via a network, via a browser or other application or via other means suitable for the purposes described herein. Data structures described herein may comprise computer files, variables, programming arrays, programming structures, or any electronic information storage schemes or methods, or any combinations thereof, suitable for the purposes described herein.

Although the present disclosure has been described hereinabove by way of non-restrictive, illustrative embodiments thereof, these embodiments may be modified at will within the scope of the appended claims without departing from the spirit and nature of the present disclosure.

What is claimed is:

1. A method of scanning an object, comprising:
defining, by a controller, a rectangular grid on a 3D representation of a surface of the object, wherein the rectangular grid defines a plurality of pulse positions distributed on the surface of the object and wherein a mesh size of the pulse positions varies at distinct positions on the rectangular grid;
positioning, by the controller, two virtual, orthogonal axes on axes of the rectangular grid, wherein an orientation of each of the two, virtual orthogonal axes varies at distinct pulse positions on the rectangular grid; and
moving, by the controller, a probe from a first pulse position to a next pulse position along a scanning path calculated as a function of orientations of the two virtual, orthogonal axes on the rectangular grid;
wherein positions of the probe along the scanning path are defined according to a combination of linear and rotational mechanical axes of a multi-axis movable support holding the probe and controlled by the controller.

2. The method of claim 1, comprising defining the two virtual, orthogonal axes in a parametric space of the surface of the object.

3. The method of claim 1, comprising defining the rectangular grid by isomorphic triangulation of the surface of the object.

4. The method of claim 3, comprising performing a smoothing of the rectangular grid defined by isomorphic triangulation of the surface of the object.

5. The method of claim 1, wherein:
the probe is moved along the scanning path in a plurality of successive probe positions corresponding to a plurality of positions and orientations of the two virtual, orthogonal axes on the rectangular grid;
wherein a distance between two nearest probe positions corresponds to a mesh size at a current position on the rectangular grid.

6. The method of claim 1, comprising:
determining a contour of the object; and
defining the rectangular grid within the contour of the object.

7. The method of claim 2, comprising defining the parametric space based on a computer-aided design file representing the object.

8. The method of claim 1, comprising:
generating a plurality of probe pulses along the scanning path of the probe;
detecting a plurality of signals resulting from the probe pulses; and
creating an image of the object from the plurality of detected signals.

9. The method of claim 1, comprising operating the probe in pulse-echo mode.

10. The method of claim 1, wherein the probe is an emitting probe facing an entry surface of the object, the method further comprising:
providing a receiving probe facing an exit surface of the object; and
controlling a synchronized scanning path of the emitting probe and of the receiving probe.

11. The method of claim 1, comprising controlling a scanning path of an array of probes as a function of the two virtual, orthogonal axes.

12. An apparatus for scanning an object, comprising:
a multi-axis movable support;
a probe mounted on the multi-axis movable support; and
a controller operably connected to the multi-axis movable support and to the probe, the controller being configured to define a rectangular grid on a 3D representation of a surface of the object, wherein the rectangular grid defines a plurality of pulse positions distributed on the surface of the object and wherein a mesh size of the pulse positions varies at distinct positions on the rectangular grid, calculate positions of two virtual, orthogonal axes on axes of the rectangular grid, wherein an orientation of each of the two, virtual orthogonal axes varies at distinct pulse positions on the rectangular grid, and control a scanning path of the probe from a first pulse position to a next pulse position as a function of orientations of the two virtual, orthogonal axes on the rectangular grid;
wherein the controller is configured to determine positions of the probe along the scanning path according to a combination of linear and rotational mechanical axes of the multi-axis movable support.

13. The apparatus of claim 12, wherein the probe is an ultrasonic probe.

14. The apparatus of claim 12, wherein the controller comprises:
a computer for calculating the position of the two virtual, orthogonal axes on the surface of the object and for providing positioning commands to the multi-axis movable support;
an encoder monitoring module for receiving probe position information from the multi-axis movable support, for receiving the position of the two virtual, orthogonal axes on the surface of the object, and for generating pulse commands; and
an ultrasonic data acquisition unit for receiving the pulse commands, for forwarding the pulse commands to the probe, for receiving detected signal information from the probe, and for forwarding detected signal information to the computer.

15. The apparatus of claim 14, wherein:
the probe is configured to generate pulses from the pulse commands, to detect signals resulting from the pulses, and to forward the detected signal information to the ultrasonic data acquisition unit; and
the computer is configured to create an image of the object from the detected signal information and to forward the image to a display.

16. The apparatus of claim 14, wherein the multi-axis movable support comprises:
a motion controller for receiving the positioning commands and for moving the probe; and
an encoder for detecting movements of the probe and for providing the probe position information.

17. The apparatus of claim 16, wherein:
the positioning commands comprise a plurality of commands for moving the multi-axis movable support about the combination of linear and rotational mechanical axes;
the apparatus comprises a plurality of encoders configured to detect movements of the probe about the combination of linear and rotational mechanical axes; and
the probe position information comprises information about position of the probe in the combination of linear and rotational mechanical axes.

18. The apparatus of claim 12, comprising:
- an emitting probe positionable facing an entry surface of the object; and
- a receiving probe positionable facing an exit surface of the object;
- wherein the controller is configured to control a synchronized scanning path of the emitting probe and of the receiving probe.

19. The apparatus of claim 12, comprising a phased array of probes mounted on the multi-axis movable support and configured to concurrently inspect a plurality of positions of pairs of virtual, orthogonal axes on the surface of the object.

20. The apparatus of claim 12, comprising a phased array of probes mounted on the multi-axis movable support and configured to steer or focus a beam on or below the surface of the object.

21. Use of the apparatus of claim 12 for non-destructive testing of the object.

\* \* \* \* \*